US008574601B2

(12) United States Patent
Kato et al.

(10) Patent No.: US 8,574,601 B2
(45) Date of Patent: Nov. 5, 2013

(54) SUSTAINED-RELEASE POLYMER MICELLE DISRUPTABLE BY HDL

(75) Inventors: Yasuki Kato, Kashiwa (JP); Mitsunori Harada, Kashiwa (JP); Miho Ohuchi, Kashiwa (JP)

(73) Assignee: Nanocarrier Co., Ltd., Kashiwa-Shi (JP)

( * ) Notice: Subject to any disclaimer, the term of this patent is extended or adjusted under 35 U.S.C. 154(b) by 0 days.

(21) Appl. No.: 13/258,797

(22) PCT Filed: Feb. 7, 2011

(86) PCT No.: PCT/JP2011/052475
§ 371 (c)(1),
(2), (4) Date: Dec. 29, 2011

(87) PCT Pub. No.: WO2011/096558
PCT Pub. Date: Aug. 11, 2011

(65) Prior Publication Data
US 2012/0093881 A1      Apr. 19, 2012

(30) Foreign Application Priority Data

Feb. 5, 2010   (JP) .................................. 2010-024323

(51) Int. Cl.
*A61K 38/02* (2006.01)
*A61K 9/00* (2006.01)

(52) U.S. Cl.
USPC .......................................... 424/400; 514/1.1

(58) Field of Classification Search
USPC ........................................................ 424/400
See application file for complete search history.

(56) References Cited

U.S. PATENT DOCUMENTS

| | | | |
|---|---|---|---|
| 5,449,513 A | 9/1995 | Yokoyama et al. | |
| 5,510,103 A | 4/1996 | Yokoyama et al. | |
| 6,153,596 A * | 11/2000 | Liotta et al. | 514/44 A |
| 6,630,171 B1 | 10/2003 | Huille et al. | |
| 2007/0196497 A1 | 8/2007 | Pouliquen et al. | |
| 2007/0218142 A1 | 9/2007 | Bignon et al. | |
| 2007/0269517 A1 | 11/2007 | Pouliquen et al. | |
| 2008/0248097 A1 * | 10/2008 | Kwon et al. | 424/450 |
| 2009/0291130 A1 | 11/2009 | Ohuchi et al. | |
| 2010/0298495 A1 | 11/2010 | Bobe et al. | |
| 2011/0052917 A1 | 3/2011 | Kataoka et al. | |

FOREIGN PATENT DOCUMENTS

| | | |
|---|---|---|
| CA | 2 718 003 | 9/2009 |
| EP | 2 077 293 A1 | 7/2009 |
| JP | 6-107565 A | 4/1994 |
| JP | 10-110019 A | 4/1998 |
| JP | 11-335267 A | 12/1999 |
| JP | 2001-504093 A | 3/2001 |
| JP | 2002-179556 A | 6/2002 |
| JP | 2002-530323 A | 9/2002 |
| JP | 2004-522717 A | 7/2004 |
| JP | 2005-336402 A | 12/2005 |
| JP | 2007-511586 A | 5/2007 |
| JP | 2007-511587 A | 5/2007 |
| JP | 2007-511588 A | 5/2007 |
| JP | 2008-214324 A | 9/2008 |
| JP | 2009-539810 A | 11/2009 |
| JP | 2009-544759 A | 12/2009 |
| WO | WO 98/16202 A2 | 4/1998 |
| WO | 02/43699 | 6/2002 |
| WO | WO 02/43699 A2 | 6/2002 |
| WO | WO 2008/010341 A1 | 1/2008 |
| WO | WO 2009/113645 A1 | 9/2009 |

OTHER PUBLICATIONS

Stone, William L. "Hydrophobic Interaction of Alkanes with Liposomes and Lipoproteins". The Journal of Biological Chemistry, vol. 250, No. 11, pp. 4363-4370. 1975. Accessed online Jul. 26, 2012.*
Rajan et al. "Modulation of protein aggregation by polyethylene glycol conjugation: GCSF as a case study", Protein Science, 15:1063-1075 (2006).*
S. Horie et al.; "Development of a micelle encapsulating dendrimer phthalocyanine in which cholesterol group is introduced into an inner core"; Drug Delivery System, vol. 24, No. 3, p. 330; 2009, with English translation.
The Extended European Search Report issued Apr. 24, 2012, in Application No. / Patent No. 11739905.5 1 1219 / 2433618 PCT/JP2011052475.
Office Action from the European Patent Office dated Jun. 10, 2013 for counterpart European patent application No. 11 739 905.5.
English translation of Office Action from Chinese Patent Office in counterpart Chinese patent application No. 201180008298.5 mailed Apr. 24, 2013.
English translation of Office Action from Taiwanese Patent Office in counterpart Taiwanese patent application No. 100104217 issued Jan. 31, 2013.

* cited by examiner

*Primary Examiner* — Richard Schnizer
*Assistant Examiner* — Audrea Buckley
(74) *Attorney, Agent, or Firm* — J-TEK Law PLLC; Jeffrey D. Tekanic (57) ABSTRACT

A pharmaceutical composition containing a drug encapsulated in a polymer micelle composition containing a first block copolymer having affinity with HDL and a second block copolymer having affinity with a lipoprotein excluding HDL, each block copolymer having a hydrophobic polymer chain segment and a hydrophilic polymer chain segment such that a plurality of block copolymers arrange radially with the hydrophobic segments directed inward and the hydrophilic segments directed outward. In the composition, a detachment of the first block copolymer is induced by HDL adhesion which forms a gap and promotes the release of a drug encapsulated, while the second block copolymer excluding an affinity with HDL controls a release speed of the drug encapsulated.

22 Claims, 4 Drawing Sheets

SUSTAINED-RELEASE POLYMER MICELLE DISRUPTABLE BY HDL

CROSS-REFERENCE

This application is the US national stage of International Patent Application No. PCT/JP2011/052475 filed on Feb. 7, 2011, which claims priority to Japanese Patent Application No. 2010-024323 filed on Feb. 5, 2010.

TECHNICAL FIELD

The present invention relates to pharmaceutical compositions containing a polymer micelle composition and to methods of using the same.

BACKGROUND ART

It is known to use block copolymers that have a hydrophilic polymer chain segment and a hydrophobic polymer chain segment as a carrier for drugs and it is also known to encapsulate a predetermined drug into a polymer micelle formed of such block copolymers (for example, Patent Document 1 or 2). A composition containing a homogeneous polymer micelle encapsulating a poorly water-soluble drug and a preparation method therefor are also known (Patent Document 3).

Patent Documents 1 and 2 each describe a method for encapsulating a drug into a micelle preliminarily formed from block copolymers in an aqueous medium by adding the drug to the micelle solution, and optionally, mixing and stirring the resulting mixture under heating and ultrasonication. Further, Patent Document 3 describes a method for preparing a polymer micelle encapsulating a drug by dissolving block copolymers and drugs in a water-miscible polar solvent and then subjecting the resulting mixture to dialysis against water.

According to these prior art references, it is understood that the use of the polymer micelle as a carrier for drugs has various advantages including a sustained release of the drug. However, in conventional polymer micelles, the drug is encapsulated into the micelle in a very stable manner, which may inhibit the drug from being released in a suitable manner.

PRIOR ART DOCUMENTS

Patent Document

[Patent Document 1] JP 06-107565 A
[Patent Document 2] U.S. Pat. No. 5,449,513 A
[Patent Document 3] JP 11-335267 A

SUMMARY OF THE INVENTION

In one aspect of the present teachings, a polymer micelle composition is disclosed that is capable of stably encapsulating and suitably releasing a drug. A pharmaceutical composition containing such a polymer micelle composition is also disclosed.

In another aspect of the present teachings, a polymer micelle composition comprises block copolymers each having a hydrophobic polymer chain segment and a hydrophilic polymer chain segment. A plurality of the block copolymers is arranged in a state in which the respective hydrophobic polymer chain segments are directed radially inward and the respective hydrophilic polymer chain segments are directed radially outward. The polymer micelle composition comprises a first block copolymer having affinity with HDL and a second block copolymer having affinity with a lipoprotein other than HDL. The hydrophobic polymer chain segment of the first block copolymer is formed of a polyamino acid including repeating units derived from a hydrophobic derivative of an amino acid. The hydrophobic derivative of the amino acids includes a derivative obtained by introducing an aromatic group and/or a sterol residue into a side chain of the amino acid. The hydrophobic polymer chain segment of the second block copolymer is also formed of a polyamino acid including repeating units derived from a hydrophobic derivative of an amino acid. However, this hydrophobic derivative of the amino acid includes a derivative obtained by introducing a hydrophobic group having a linear or branched structure into a side chain of the amino acid. Detachment of the first block copolymers having affinity with HDL is induced by HDL adhesion attributed to the affinity. A gap in polymer micelle forms as a result of this detachment, thereby promoting the release of a drug encapsulated within the polymer micelle. The drug may be selected from the group consisting of water-soluble physiologically active polypeptides and proteins, each having a molecular weight of 1,500 or more. After a gap in the polymer micelle has been formed, the second block copolymers having affinity with a lipoprotein other than HDL cause the size of the gap to decrease, thereby again suppressing the release of the encapsulated drug. This gap-repairing mechanism enables the release speed of the drug to be controlled by suitably selecting the second block polymer.

In another aspect of the present teachings, a polymer micelle composition comprises block copolymers, each having a hydrophobic polymer chain segment and a hydrophilic polymer chain segment. A plurality of the block copolymers is arranged in a state in which the respective hydrophobic polymer chain segments are directed radially inward and the respective hydrophilic polymer chain segments are directed radially outward. The polymer micelle composition comprises a first block copolymer having affinity with HDL as one of the block copolymers. The hydrophobic polymer chain segment of the first block copolymer is formed of a polyamino acid including repeating units derived from introducing a sterol residue into a side chain of the amino acid. The hydrophilic polymer chain segment of the first block copolymer is comprised of poly(ethylene glycol). Detachment of the first block copolymer having affinity with HDL is induced by HDL adhesion attributed to the affinity. A gap in the polymer micelle forms as a result of this detachment, thereby promoting release of a drug encapsulated within the polymer micelle. The drug may be selected from the group consisting of water-soluble physiologically active polypeptides and proteins, each having a molecular weight of 1,500 or more.

In another aspect of the present teachings, a pharmaceutical composition is disclosed that comprises the above-mentioned polymer micelle composition and a drug encapsulated in the polymer micelle. Again, the drug is preferably selected from the group consisting of water-soluble physiologically active polypeptides and proteins, each having a molecular weight of 1,500 or more.

Thus, the present teachings provide a polymer micelle composition capable of stably encapsulating and suitably releasing a drug, and a pharmaceutical composition that contains such a polymer micelle composition.

DETAILED DESCRIPTION OF THE EMBODIMENTS

A. Polymer Micelle Composition

A polymer micelle composition of the present teachings preferably includes block copolymers, each having a hydrophobic polymer chain segment and a hydrophilic polymer chain segment. A plurality of the block copolymers are arranged in a state in which the respective hydrophobic polymer chain segments are directed radially inward and the respective hydrophilic polymer chain segments are directed radially outward. The polymer micelle composition includes a first block copolymer having affinity with high-density lipoprotein (HDL) (hereinafter, sometimes referred to as "block copolymer with HDL affinity") as one of the block copolymers. In such a polymer micelle composition, detachment of the first block copolymer with HDL affinity is induced by HDL adhesion attributed to the affinity, which detachment causes a gap to be formed in the polymer micelle. A drug encapsulated in the polymer micelle can then be released through the gap(s).

The adhesion property of the polymeric micelle to HDL may be confirmed by observing the presence of block copolymers in an HDL fraction after incubating the polymer micelle composition in the presence of HDL (for example, in plasma) and then purifying the HDL fraction. The "hydrophobic polymer chain segment" and the "hydrophilic polymer chain segment" may have any suitable hydrophobic degree and hydrophilic degree, respectively, as long as a micelle, in which a plurality of block copolymers each having those two segments are arranged in the above-mentioned state, can be formed in an aqueous medium.

Figure 1:
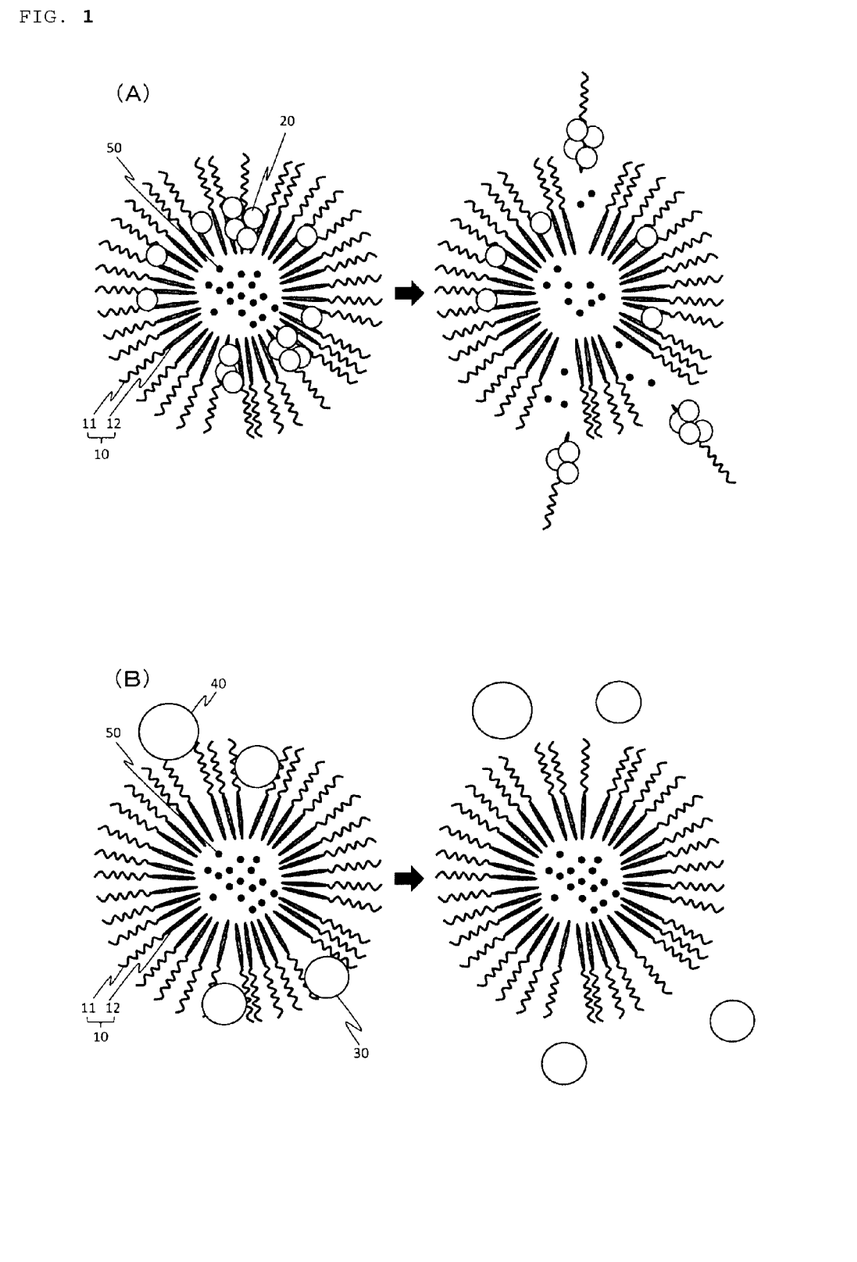
FIGS. 1(A) and 1(B) are conceptual diagrams illustrating interactions between a polymer micelle composition of the present teachings and lipoproteins.

Although not wishing to be bound by theory, a possible reason for the increased release rate of a drug from the polymer micelle composition is described below. As illustrated in FIG. 1(A), in blood, HDL 20, which has an average particle diameter as small as about 10 nm, can easily penetrate or infiltrate into the interior (hydrophobic polymer chain segment region) of a polymer micelle including first block copolymers 10 having HDL affinity, each of which includes a hydrophilic polymer chain segment 11 and a hydrophobic polymer chain segment 12. The hydrophobic polymer chain segment region of the first block copolymers 10 having HDL affinity interacts with (i.e. adheres to) HDL 20, which has penetrated or infiltrated into the hydrophobic polymer chain segment region of the micelle, due to the HDL affinity of the hydrophobic polymer chain segment region, as illustrated in the left-side drawing of FIG. 1(A). Consequently, such first block copolymer 10 is preferentially detached from the polymer micelle due to its adhesion to HDL 20, as illustrated in the right-side drawing of FIG. 1(A). As a result, one or more gaps are formed in the polymer micelle structure, which gap(s) facilitate(s) the release of encapsulated drug 50.

Further, the polymer micelle may readily disintegrate at this time, which would further promote the release of the drug 50. Meanwhile, as illustrated in FIG. 1(B), low-density lipoprotein (LDL) 30, which has a relatively large average particle diameter of about 26 nm, and very-low-density lipoprotein (VLDL) 40, which has a particle diameter equal to or greater than the diameter of the LDL, can not easily penetrate or infiltrate into the hydrophobic polymer chain segment region of the polymer micelle. Thus, in view of the fact that the first block copolymers with HDL affinity 10 inherently only weakly interact with lipoproteins other than HDL, detachment of the first block copolymers from the polymer micelle caused by adhesion to lipoproteins other than HDL is expected to rarely occur.

The drug to be encapsulated in the polymer micelle composition preferably may be selected from the group consisting of water-soluble physiologically active polypeptides and proteins, each having a molecular weight of 1,500 or more. Such a drug has a relatively large size and hence can not easily leak through small gaps between block copolymers in conventional polymer micelles. Thus, such a drug may not be sufficiently released and may be eliminated from the blood stream together with the micelles.

On the other hand, the polymer micelle compositions according to the present teachings exhibit a sustained-release performance of a drug due to its encapsulation in micelles, while also exhibiting a suitable release of such drug having a relatively large size as compared to conventional polymer micelles.

Further, as will be described below, in certain polymer micelle compositions according to the present teachings, a second block copolymer having affinity with one or more lipoproteins other than HDL such as LDL or VLDL (hereinafter, sometimes referred to as "block copolymer without HDL affinity") may also be further incorporated into the polymer micelle in order to control or adjust the release rate of the encapsulated drug.

The hydrophobic polymer chain segment in the first block copolymer with HDL affinity may be formed of a polyamino acid. The polyamino acid includes repeating units derived from a hydrophobic derivative of an amino acid obtained by introducing a hydrophobic group having a cyclic structure into a side chain of the amino acid. The hydrophobic derivative of an amino acid having a cyclic structure is preferably a hydrophobic derivative of an acidic amino acid such as aspartic acid and glutamic acid, and the hydrophobic group having a cyclic structure may be introduced into a carboxyl group in the side chain of the acidic amino acid.

The hydrophobic group having a cyclic structure may be a group having a monocyclic structure or a group having a polycyclic structure, and for example, may be an aromatic group, an alicyclic group, or a sterol residue. The hydrophobic group is preferably a $C_4$ to $C_{16}$ alkyl group having a cyclic structure, a $C_6$ to $C_{20}$ aryl group, a $C_7$ to $C_{20}$ aralkyl group, or a sterol residue. As used herein, the term "sterol" means a natural, semisynthetic, or synthetic compound based on a cyclopentanone hydrophenanthrene ring ($C_{17}H_{28}$) and derivatives thereof. For example, natural sterols are exemplified by cholesterol, cholestanol, dihydrocholesterol, cholic acid, campesterol, and sitosterol. The semisynthetic or synthetic compounds may be, for example, synthetic precursors of the natural sterol (as necessary, encompassing compounds in which some or all of, if present, certain functional groups, hydroxy groups have been protected with a hydroxy protective group known in the art, or compounds in which a carboxyl group has been protected with carboxyl protective group). The sterol derivative may have a $C_6$ to $C_{12}$ alkyl group or a halogen atom such as chlorine, bromine, and fluorine introduced into a cyclopentanone hydrophenanthrene ring as long as the object of the present teachings is not adversely affected. The cyclopentanone hydrophenanthrene ring may be saturated or partially unsaturated.

The hydrophobic polymer chain segment in the first block copolymer with HDL affinity may include not only repeating units derived from a hydrophobic derivative of an amino acid having a cyclic structure but also other repeating units as long as the effects of the present teachings are exhibited. Examples of such other repeating units include: repeating units derived from an acidic amino acid such as glutamic acid and aspartic acid, and for example, a hydrophobic derivative obtained by introducing a $C_4$ to $C_{16}$ unsubstituted or substituted linear or branched alkyl group into the acidic amino acid.

The content of the repeating units derived from the hydrophobic derivative of an amino acid having a cyclic structure is preferably 10 to 100 mol %, more preferably 20 to 80 mol % with respect to the total (100 mol %) of the repeating units that form the hydrophobic polymer chain segment in the first block copolymer with HDL affinity. The above-mentioned contents can suitably provide the necessary amount of affinity with HDL.

Examples of the hydrophilic polymer chain segment in the first block copolymer with HDL affinity include poly(ethylene glycol), polysaccharide, poly(vinyl pyrrolidone), poly(vinyl alcohol), poly(acrylic amide), poly(acrylic acid), poly(methacrylic amide), poly(methacrylic acid), poly(methacrylic acid ester), poly(acrylic acid ester), polyamino acid, poly(malic acid), and derivatives thereof. Specific examples of the polysaccharide include starch, dextran, fructan, and galactan.

In the first block copolymer with HDL affinity, the hydrophilic polymer chain segment and the hydrophobic polymer chain segment may be linked to each other by a known linking group. Examples of the linking group include an ester bond, an amide bond, an imino group, a carbon-carbon bond, and an ether bond. The end opposite to the end at the side of the hydrophilic polymer chain segment in the hydrophobic polymer chain segment and the end opposite to the end at the side of the hydrophobic polymer chain segment in the hydrophilic polymer chain segment may be subjected to any suitable chemical modification as long as formation of a polymer micelle is not adversely affected.

The first block copolymer with HDL affinity may include a hydrophilic polymer chain segment of poly(ethylene glycol) and a hydrophobic polymer chain segment formed of a polyamino acid including repeating units derived from a hydrophobic derivative of an amino acid. The hydrophobic derivative of the amino acid may be a derivative obtained by introducing a sterol residue into a side chain of the amino acid.

The first block copolymer with HDL affinity may be represented by each of the following general formulae (I) and (II). The polymer micelle composition of the present teachings may include two or more kinds of first block copolymers with HDL affinity.

(I)

(II)

In each of the above-mentioned formulae, $R^1$ and $R^3$ each independently represent a hydrogen atom or a lower alkyl group unsubstituted or substituted with an optionally protected functional group;
$R^2$ represents a hydrogen atom, a saturated or unsaturated $C_1$ to $C_{29}$ aliphatic carbonyl group, or an arylcarbonyl group;
$R^4$ represents a hydroxyl group, a saturated or unsaturated $C_1$ to $C_{30}$ aliphatic oxy group, or an aryl-lower alkyloxy group;
Each $R^5$ represents —O— or —NH—;
Each $R^6$ represents a hydrogen atom, a $C_4$ to $C_{16}$ alkyl group having a cyclic structure unsubstituted or substituted with an amino group or a carboxyl group, a $C_6$ to $C_{20}$ aryl group, a $C_7$ to $C_{20}$ aralkyl group, or a steryl group;
$R^7$ and $R^8$ each independently represent a methylene group or an ethylene group;
n represents an integer in the range of 10 to 2,500;
x represents an integer in the range of 10 to 300;
m represents an integer in the range of 0 to 300 (provided that, when m is 1 or more, a repeating unit with a number of repetitions of x and a repeating unit with a number of repetitions of m are bound to each other in any suitable order, each $R^6$ is independently selected in the respective repeating units in one block copolymer and are present at random, and 10% or more of all $R^6$'s are each independently selected from a $C_4$ to $C_{16}$ alkyl group having a cyclic structure unsubstituted or substituted with an amino group or a carboxyl group, a $C_6$ to $C_{20}$ aryl group, a $C_7$ to $C_{20}$ aralkyl group, and a steryl group);
$L^1$ represents a linking group selected from the group consisting of —NH—, —O—, —O—Z—NH—, —CO—, —CH_2—, —O—Z—S—Z—, and —OCO—Z—NH— (where each Z independently represents a $C_1$ to $C_6$ alkylene group); and
$L^2$ represents a linking group selected from —OCO—Z—CO— and —NHCO—Z—CO— (where each Z again represents a $C_1$ to $C_6$ alkylene group).

The $C_6$ to $C_{20}$ aryl group and the $C_7$ to $C_{20}$ aralkyl group are preferably exemplified by a phenyl group, a naphthyl group, a tolyl group, a xylyl group, a benzyl group, and a phenethyl group, more preferably a benzyl group. Further, a sterol from which the steryl group is derived is preferably exemplified by cholesterol, cholestanol, and dihydroxycholesterol, more preferably cholesterol.

Preferably, n in each of the above-mentioned formulae represents an integer in the range of 10 to 1,000, more preferably 20 to 600, particularly preferably 50 to 500.

Preferably, x and m in each of the above-mentioned formulae each represent an integer in the range of 20 to 200, more preferably 30 to 100.

Examples of the optionally protected functional group include a hydroxyl group, an acetal, a ketal, an aldehyde, a sugar residue, a maleimide group, a carboxyl group, an amino group, a thiol group, and an active ester. In case $R^1$ and $R^3$ each represent a lower alkyl group substituted with an optionally protected functional group, the hydrophilic polymer chain segment may be prepared, for example, in accordance with the methods described in WO 96/33233 A1, WO 96/32434 A1, and WO 97/06202 A1. The lower alkyl group means a linear or branched alkyl group having, for example, 7 or less, preferably 4 or less carbon atoms.

The first block copolymer with HDL affinity may be obtained, for example, by coupling a polymer having a hydrophilic polymer chain to a polymer having a polyamino acid chain using a known method, each of which has not been subjected to any treatment or has been purified so as to achieve a narrow molecular weight distribution, if necessary. The block copolymer of the general formula (I) may also be formed, for example, by carrying out anionic living polymerization using an initiator capable of giving $R^1$ to form a polyethylene glycol chain, then introducing an amino group at the side of the growing end, and polymerizing an N-carboxylic anhydride (NCA) of a protected amino acid such as β-benzyl-L-aspartate or γ-benzyl-L-glutamate from the amino end.

A specific example of a method of manufacturing the first block copolymer with HDL affinity is described below. Either (i) N-carboxy-β-benzyl-L-aspartic anhydride (BLA-NCA) or (ii) N-carboxy-γ-benzyl-L-glutamic anhydride (BLG-NCA) is added and subjected to a reaction using, as an initiator, polyethylene glycol, which is protected at one end and has an amino group at the other end, such as MeO-PEG-$CH_2CH_2CH_2$—$NH_2$, in a dehydrated organic solvent so as to achieve a desired degree of polymerization (number of amino acid units), to thereby afford (i) polyethylene glycol-co-polyaspartic acid benzyl ester or (ii) polyethylene glycol-co-polyglutamic acid benzyl ester. In addition, one end of the resultant block copolymer is acetylated with acetyl chloride or acetic anhydride, then subjected to alkali hydrolysis to remove a benzyl group, and converted into polyethylene glycol-co-polyaspartic acid or polyethylene glycol-co-polyglutamic acid. After that, benzyl alcohol is added to the organic solvent so as to achieve a desired esterification ratio, and the reaction is carried out in the presence of a condensation agent such as N—N'-dicyclohexyl carbodiimide (DCC) or N—N'-diisopropyl carbodiimide (DIPCI) to afford a block copolymer partially having a benzyl ester.

When the reaction is performed using cholesterol in place of benzyl alcohol, polyethylene glycol-co-polyaspartic acid cholesterol ester and polyethylene glycol-co-polyglutamic acid cholesterol ester may be prepared.

Another specific example of a method of manufacturing the first block copolymer with HDL affinity includes introducing a hydrophobic side chain through an amide bond. In this manufacturing method, one end of the polyethylene glycol-co-polyaspartic acid benzyl ester or polyethylene glycol-co-polyglutamic acid benzyl ester is acetylated in the same manner as described above. Then, a benzyl group is removed by alkali hydrolysis and the generated carboxyl group is subjected to a reaction with a hydrophobic side chain having an amino group. Alternatively, polyethylene glycol-co-polyaspartic acid benzyl ester or polyethylene glycol-co-polyglutamic acid benzyl ester and a compound having a primary amine are subjected to a reaction and then subjected to aminolysis to convert an ester bond into an amide bond. This allows the introduction of a hydrophobic side chain through an amide bond. In addition, a poly(amino acid derivative) segment including a hydrophobic side chain having a hydrophobic group, whose end has been substituted with an amino group, and a hydrophobic side chain without amino group substitution may also be obtained by adding a primary amine such as 1-octylamine to polyethylene glycol-co-polyaspartic acid benzyl ester to the organic solvent so as to achieve a desired amidation ratio, subjecting the mixture to a reaction for a predetermined period of time, and then adding a large excess amount of 1,8-diaminooctane or the like to an unconverted benzyl ester.

The first block copolymer with HDL affinity has an HDL transfer rate, which is determined as described below, of 30% or more owing to its affinity with HDL. The first block copolymer with HDL affinity preferably has an HDL transfer rate of 40% or more, more preferably 45% or more, particularly preferably 50% or more.

[Method of Determining HDL Transfer Rate]

Various block copolymers are used to form a plurality of polymer micelles encapsulating lysozyme, and the polymer micelles are incubated in plasma at 37° C. for 24 hours. After that, the respective lipoprotein fractions are purified and collected. The concentration of the respective block copolymers in each of the collected VLDL, LDL, HDL, and residual fractions is measured. Then, the content (on a weight basis) of the respective block copolymers in each of the fractions is calculated based on the volume and block copolymer concentration in each of the fractions. The resultant value is inserted into the following equation to determine the HDL transfer rate of the particular fraction.

HDL transfer rate (%)=Block copolymer content in HDL fraction/Total of block copolymer contents in all fractions×100

In determining the HDL transfer rate, the first block copolymer with HDL affinity is preferably present in a higher amount in the HDL fraction than in other lipoprotein fractions (excluding a chylomicron fraction). That is, it is preferred that the content of the first block copolymer with HDL affinity in the HDL fraction is the highest as compared to the contents of the first block copolymer with HDL affinity in the other fractions, i.e., the VLDL, LDL, and residual fractions.

As was mentioned above, polymer micelle compositions according to the present teachings may also include a second block copolymer without HDL affinity as one of the block copolymers forming the polymer micelle. It is difficult to preferentially detach block copolymers without HDL affinity from the polymer micelle. This is because lipoproteins other than HDL can not readily penetrate or infiltrate into the hydrophobic polymer chain segment region of the polymer micelle due to their large sizes. Thus, when the polymer micelle composition is prepared with a mixture of first block copolymers with HDL affinity and second block copolymers without HDL affinity, gap formation due to the detachment of the first block copolymers with HDL affinity may be suppressed. In the alternative, in some cases, gap formation may be promoted owing to a reduction in hydrophobic interaction between the block copolymers that form the polymer micelle composition. As described above, the release rate of an encapsulated drug from the polymer micelle composition may be controlled or modified by changing the relative amounts of the first block copolymer with HDL affinity and the second block copolymer without HDL affinity. That is, in this aspect of the present teachings, polymer micelles having selectively disruptable properties, which have been difficult to prepare in the past, are possible. Further, it is possible to control or adjust of the disintegration speed of the polymer micelle by suitably selecting the first and second block copolymers.

The hydrophobic polymer chain segment in the second block copolymer without HDL affinity may be formed of a polyamino acid including repeating units derived from a hydrophobic derivative of an amino acid obtained by introducing a hydrophobic group having a linear or branched structure into a side chain of the amino acid. The hydrophobic derivative of the amino acid is preferably a hydrophobic derivative of an acidic amino acid, more preferably aspartic acid and/or glutamic acid.

The hydrophobic group having a linear or branched structure is exemplified by a $C_4$ to $C_{18}$ unsubstituted or substituted linear or branched alkyl group, a $C_4$ to $C_{18}$ unsubstituted or substituted linear or branched alkenyl group, and a $C_4$ to $C_{18}$ unsubstituted or substituted linear or branched alkynyl group, preferably a $C_4$ to $C_{18}$ unsubstituted or substituted linear or branched alkyl group.

As for the hydrophilic polymer chain segment in the second block copolymer without HDL affinity, the same hydrophilic polymers as were described above for the hydrophilic polymer chain segment in the first block copolymer with HDL affinity may be used. Further, the end modification of each of the hydrophilic polymer chain segment and the hydrophobic polymer chain segment in the second block copolymer without HDL affinity and the linking of those segments also may be the same as described in the above paragraphs relating to the first block copolymer with HDL affinity.

The second block copolymer without HDL affinity may be represented by each of the following general formulae (III) and (IV):

$$R^9\text{—}(OCH_2CH_2)_p\text{—}L^3\text{—}(COCHNH)_q\text{—}(COR^{16}CHNH)_r\text{—}R^{10} \quad \text{(III)}$$
$$\begin{array}{cc} R^{15} & C\text{=}O \\ C\text{=}O & R^{13} \\ R^{13} & R^{14} \\ R^{14} & \end{array}$$

$$R^{11}\text{—}(OCH_2CH_2)_p\text{—}L^4\text{—}(NHCHCO)_q\text{—}(NHCHR^{16}CO)_r\text{—}R^{12} \quad \text{(IV)}$$
$$\begin{array}{cc} R^{15} & C\text{=}O \\ C\text{=}O & R^{13} \\ R^{13} & R^{14} \\ R^{14} & \end{array}$$

In each of the above-mentioned formulae, $R^9$ and $R^{11}$ each independently represent a hydrogen atom or a lower alkyl group unsubstituted or substituted with an optionally protected functional group;

$R^{10}$ represents a hydrogen atom, a saturated or unsaturated $C_1$ to $C_{29}$ aliphatic carbonyl group, or an arylcarbonyl group;

$R^{12}$ represents a hydroxyl group, a saturated or unsaturated $C_1$ to $C_{30}$ aliphatic oxy group, or an aryl-lower alkyloxy group;

Each $R^{13}$ represents —O— or —NH—;

Each $R^{14}$ represents a hydrogen atom, a $C_4$ to $C_{18}$ linear or branched alkyl group unsubstituted or substituted with an amino group or a carboxyl group;

$R^{15}$ and $R^{16}$ each independently represent a methylene group or an ethylene group;

p represents an integer in the range of 10 to 2,500;

q represents an integer in the range of 10 to 300;

r represents an integer in the range of 0 to 300 (provided that, when r is 1 or more, a repeating unit with a number of repetitions of q and a repeating unit with a number of repetitions of r are bound to each other in any suitable order, each $R^{14}$ is independently selected in the respective repeating units in one block copolymer and are present at random, and 40% or less of all $R^{14}$'s are hydrogen atom);

$L^3$ represents a linking group selected from the group consisting of —NH—, —O—, —O—Z—NH—, —CO—, —CH$_2$—, —O—Z—S—Z—, and —OCO—Z—NH— (where each Z independently represents a $C_1$ to $C_6$ alkylene group); and $L^4$ represents a linking group selected from —OCO—Z—CO— and —NHCO—Z—CO— (where Z again represents a $C_1$ to $C_6$ alkylene group).

Preferably, p in each of the above-mentioned formulae represents an integer in the range of 10 to 1,000, more preferably 20 to 600, particularly preferably 50 to 500. Preferably, q and r in each of the above-mentioned formulae each represent an integer in the range of 20 to 200, more preferably 30 to 100.

The optionally protected functional group is as described in the above paragraph relating to each of the formulae (I) and (II).

The HDL transfer rate of the second block copolymer without HDL affinity may be less than 30%, preferably 25% or less, more preferably 20% or less. That is, the second block copolymer may, in fact, have a certain amount of affinity to HDL, but its affinity to HDL is less than the affinity of the first block copolymer to HDL. Therefore, it should be understood that the expression "without HDL affinity" is broad enough to encompass embodiments of the second block copolymer having less affinity to HDL than the first block copolymer.

The content ratio of the first block copolymer with HDL affinity to the second block copolymer without HDL affinity in the polymer micelle composition of the present teachings (i.e. first block copolymer:second block copolymer weight ratio) may be suitably selected depending on the intended use of the polymer micelle composition, the preferred HDL transfer rate of each of the first and second block copolymers, etc. The above-defined content ratio may be, for example, in the range of 1:99 to 99:1, preferably in the range of 3:97 to 97:3, more preferably in the range of 15:85 to 85:15, or even more preferably in the range of 40:60 to 60:40. As described above, the weight ratio of the first block copolymer with HDL affinity with respect to the total weight of the first and second block copolymers in the polymer micelle composition may be, for example, 60% or less, 50% or less, 40% or less, 20% or less, 10% or less, 5% or less, 2% or less, or 1% or less. The polymer micelle tends to disintegrate more readily thereby increasing release rate of the encapsulated drug, as the content ratio of the first block copolymer with HDL affinity is increased. Consequently, the disintegration of the polymer micelle and the attendant release of a drug tend to be increasingly suppressed when the content ratio of the first block copolymer with HDL affinity is decreased.

B. Pharmaceutical Composition

Pharmaceutical compositions of the present teachings include the polymer micelle composition described in the above section A and a drug encapsulated in the polymer micelle composition. The drug is preferably selected from the group consisting of water-soluble physiologically active polypeptides and proteins. In addition, the drug preferably has a molecular weight of 1,500 or more, more preferably 2,000 or more. Preferred examples of the physiologically active polypeptides and proteins include: interferons α, β, and γ; erythropoietin; G-CSF; growth hormone; interleukins; tumor necrosis factor; granulocyte-macrophage colony-stimulating factor; macrophage colony-stimulating factor; hepatocyte growth factor; TGF-β superfamily; EGF; FGF; IGF-I; and blood coagulation factors typified by Factor VII. Further, as long as their activities are not impaired, derivatives of the above-mentioned proteins, more specifically, proteins having substitutions, additions, or deletions in one or more amino acids, may be used as medicaments.

In addition or in the alternative, the drug may be a poorly water-soluble drug having a water solubility of 100 µg/mL or less. Examples of poorly water-soluble drugs include: anti-cancer agents such as paclitaxel, topotecan, camptothecin, cisplatin, daunorubicin hydrochloride, methotrexate, mitomycin C, docetaxel, vincristine sulfate, and derivatives thereof; polyene-based antibiotics such as amphotericin B and nystatin; and lipophilic drugs such as prostaglandins and derivatives thereof. Such poorly water-soluble drugs have a relatively small size but it may be difficult to release them from conventional polymer micelle compositions owing to their high hydrophobicity. On the other hand, the pharmaceutical composition of the present teachings also can be advantageously utilized to promote the release of such poorly water-soluble drug as compared to conventional polymer micelle compositions.

The amount of the drug to be encapsulated may be suitably selected depending on the intended use of the pharmaceutical composition, etc. The amount of the drug to be used is generally 0.01 to 50 wt %, preferably 0.1 to 10 wt % with respect to the total weight of the block copolymers in the polymer micelle composition.

The particle diameter of the polymer micelle encapsulating the drug is not particularly limited as long as it has a size capable of being administered into a living body. The particle diameter is preferably 10 µm or less, more preferably 5 µm or less. In particular, when the polymer micelle is used in intravenous administration, the particle diameter is preferably 500 nm or less, more preferably 300 nm or less.

The pharmaceutical composition may be prepared according to the following example. First, the above-mentioned block copolymers are dissolved in an organic solvent. If necessary, the organic solvent may be removed by subjecting the resultant solution to air drying, e.g., drying to form a film under a nitrogen gas stream atmosphere and further drying under reduced pressure as necessary. A solution containing the drug to be encapsulated is then added to and mixed with the thus-treated block copolymers. Then, a polymer micelle is formed from the resultant mixed solution with the resulting encapsulation of the drug.

Examples of the organic solvent include: non-water-miscible organic solvents such as dichloromethane, chloroform, diethyl ether, dibutyl ether, ethyl acetate, and butyl acetate; water-miscible organic solvents such as methanol, ethanol, propyl alcohol, isopropyl alcohol, dimethylsulfoxide, dimethylformamide, dimethylacetamide, acetonitrile, acetone, and tetrahydrofuran; and mixed solvents thereof.

The polymer micelle encapsulating a drug may be formed, for example, by stirring a mixed solution of block copolymers and a drug while applying ultrasonic energy to the solution. The ultrasonic irradiation may be performed, for example, using a biodisruptor (manufactured by NIHONSEIKI KAISHA LTD.).

C. Method of Controlling the Release Rate of the Drug from Pharmaceutical Composition As was noted above, the content ratio of the first block copolymer with HDL affinity can be changed relative to the total weight of the block copolymers in the polymer micelle composition in the pharmaceutical composition described in the above section B. The first block copolymer with HDL affinity is capable of promoting the release of the drug from the polymer micelle. Thus, the content ratio of the first block copolymer with HDL affinity may be changed to control or adjust the release rate of the drug from the polymer micelle.

For example, the content ratio of the first block copolymer with HDL affinity with respect to the total weight of the block copolymers in the polymer micelle composition (content of first block copolymer/total content of block copolymers weight ratio) is set in the range of greater than 0/100 to 100/100 or less, preferably 1/100 to 100/100. More specifically, the content ratio of the first block copolymer with HDL affinity with respect to the second block copolymer without HDL affinity in the polymer micelle composition (first block copolymer:second block copolymer weight ratio) is set, for example, in the range of 1:99 to 99:1, preferably in the range of 3:97 to 97:3, more preferably in the range of 15:85 to 85:15, or even more preferably in the range of 40:60 to 60:40. An increased release rate of the drug results when the content ratio of the first block copolymer with HDL affinity is large, whereas the release rate of the drug is reduced when the content ratio of the first block copolymer is small.

EXAMPLES

In the following description, for the purpose of simplifying the expression, for example, when a block copolymer includes a hydrophilic polymer chain segment comprised of a PEG chain having an average molecular weight of 10,000 and a hydrophobic polymer chain segment comprised of a polyamino acid chain having 40 amino acid residues on average, and also has an introduction percentage of benzyl groups into side chains of the polyamino acid chain of about 65%, the expression "block copolymer (10-40, 65% Bn)" is used. Similarly, when the hydrophobic groups to be introduced into the side chain of the polyamino acid chain are an octyl group and a cholesteryl group, the expressions "block copolymer (10-40, 65% C8)" and "block copolymer (10-40, 65% Chol)" are used, respectively. The introduction percentage of hydrophobic groups of about 65% encompasses 62 to 68%.

Reference Example 1

Preparation of Polymer Micelles Encapsulating Lysozyme

The block copolymers described in the following general formula (V) and Table 1 were used as block copolymers. Each of the block copolymers was weighed in a vial and purified water was added thereto so as to achieve a polymer concentration of 5 mg/mL. Then, the polymer solutions were vigorously stirred at 4° C. overnight. The polymer solutions were subjected to ultrasonic irradiation (in an ice water bath, Low, interval of 1 second, 10 minutes) using a biodisruptor (High Power Unit manufactured by NIHONSEIKI KAISHA LTD.) and then treated with a 0.22-µm membrane filter. Thus, empty micelle solutions each having a polymer concentration of 5 mg/mL are obtained. To each of the empty micelle solutions (0.6 mL) were added a 1 mg/mL lysozyme solution (0.15 mL) so as to achieve a concentration of 5% (w/w) with respect to the polymer, a 200 mM sodium phosphate buffer (pH 6), and purified water. The resultant mixtures were adjusted with 0.1 N HCl so as to finally achieve a polymer concentration of 3 mg/mL, a lysozyme concentration of 0.15 mg/mL, and a composition of a 20 mM sodium phosphate buffer as well as a pH of 6. The solutions were inverted and swirled two or three times and then left to stand still at 4° C. overnight. The micelles each encapsulating lysozyme prepared as described above were warmed to room temperature, and then they were used.

(V)

In the above-mentioned formula, a glutamic acid unit and its hydrophobic derivative unit may be bound to each other in any suitable order and are present at random in one block copolymer.

TABLE 1

| Block copolymer | PEG molecular weight | $R_{17}$ | t |
|---|---|---|---|
| PEG-pGlu (10-40, 60% Bn) | 10,000 | Benzyl group | 24 |
| PEG-pGlu (10-40, 30% Chol) | 10,000 | Cholesteryl group | 12 |
| PEG-pGlu (10-40, 60% C8) | 10,000 | Octyl group | 24 |
| PEG-pGlu (10-40, 60% C12) | 10,000 | Dodecyl group | 24 |
| PEG-pGlu (10-40, 60% C16) | 10,000 | Hexadecyl group | 24 |

Reference Example 2

HDL Transfer Rate

Figure 2:
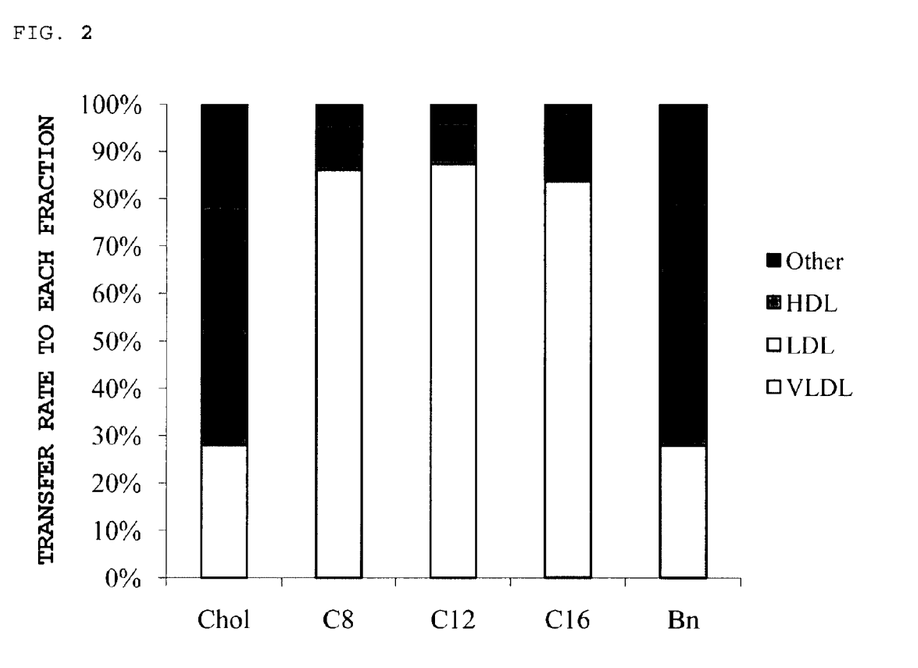
FIG. 2 is a graph illustrating the ratios of polymer contents in respective lipoprotein fractions.

The polymer micelles each encapsulating lysozyme prepared in Reference Example 1 were used to determine the HDL transfer rate of each of the block copolymers. A specific experimental method is described below. To 810 μL of rat plasma, which was stored at −80° C. after centrifugation of blood collected with heparin from 8-week-old male Wistar rats, was added 90 μL of the respective polymer micelles encapsulating lysozyme, and the mixture was incubated at 37° C. for 24 hours (final lysozyme concentration: 15 μg/mL, final polymer concentration: 300 μg/mL). The mixture was then subjected to ultracentrifugation under the conditions of 45,000 rpm (about 100,000 g), 15 minutes, and 4° C. (Rotar: MLA-130, Centrifuge tube: thick-walled polyallomer tube) using an "OptimaMAX" (trade name) (manufactured by Beckman) in accordance with the protocol of Axis-Shield Density Gradient Media downloadable from http://www.axis-shield-density-gradient-media.com/CD2009/macromol/M07.pdf. Then, a chylomicron fraction as the uppermost layer was removed from the plasma after the ultracentrifugation. After that, 180 μL of "Optiprep" (trade name) (manufactured by Axis-Shield) in a 1/4 volume of the plasma were added to 720 μL of the plasma and mixed, and the mixture was subjected to ultracentrifugation under the conditions of 85,000 rpm (about 350,000 g), 3 hours, and 16° C. During the ultracentrifugation, balance adjustment was carried out using a 0.85% (w/v) NaCl/10 mM 2-[4-(2-hydroxyethyl)-1-piperazinyl]-ethanesulfonic acid (HEPES) buffer (pH 7.4). After the ultracentrifugation, VLDL, LDL, HDL, and residual (other) fractions were collected and the block copolymer concentration in each of the fractions was measured using a PEG-ELISA kit (manufactured by Life Diagnostics). Based on the resultant polymer concentration and the volume of each of the fractions, the content of the block copolymer in each of the fractions and its ratio (i.e., transfer rate of block copolymer to each fraction) were calculated. FIG. 2 shows the results.

As can be seen from FIG. 2, both of PEG-pGlu (10-40, 60% Bn) and PEG-pGlu (10-40, 30% Chol) had an HDL transfer rate of 50% or more and showed high HDL affinity. On the other hand, all of PEG-pGlu (10-40, 60% C8), PEG-pGlu (10-40, 60% C12), and PEG-pGlu (10-40, 60% C16) had an HDL transfer rate of less than 20% and exhibited higher affinity with lipoproteins other than HDL, such as LDL and VLDL.

Example 1

Rat Intravenous Administration Test of Polymer Micelle Encapsulating G-CSF (1) PEG-pGlu (10-40, 30% Chol)

PEG-pGlu (10-40, 30% Chol) was used as a block copolymer. The block copolymer was weighed in a vial. A 20 mM 2-morpholinoethanesulfonic acid monohydrate (MES) buffer (pH 5) was added thereto so as to achieve a polymer concentration of 2 mg/mL and the mixture was vigorously stirred at 4° C. overnight. The polymer solution was subjected to ultrasonic irradiation (in an ice water bath, Low, interval of 1 second, 10 minutes) using a biodisruptor (High Power Unit manufactured by NIHONSEIKI KAISHA LTD.) and then treated with a 0.22-μm membrane filter. Thus, an empty micelle solution having a polymer concentration of 2 mg/mL was obtained. To the resultant empty micelle solution (6 mL) was added a 300 μg/mL G-CSF solution (2 mL) so as to achieve a concentration of 5% (w/w) with respect to the polymer and the mixture was inverted and swirled and then left to stand still at 4° C. overnight. After that, the solution was purified and concentrated by ultrafiltration using an Amicon® Ultra (trade name) (manufactured by Millipore Corporation, cutoff molecular weight: 100,000), and the medium was replaced with a 10% (w/w) sucrose aqueous solution. The collected polymer micelles encapsulating G-CSF were stored at −80° C. and thawed at room temperature before use.

The solution of the polymer micelles encapsulating G-CSF obtained above was administered to male Wistar rats via the tail vein. The dosage was 100 μg/kg of body weight and the number of animals for the sample was three. Blood was collected with a heparin-treated syringe from the jugular vein under ether anesthesia 5 minutes, 1 hour, 6 hours, 1 day, 2 days, and 3 days after the administration. The plasma G-CSF concentration was measured using a G-CSF-ELISA kit (manufactured by RayBiotech, Inc.).

(2) PEG-pGlu (10-40, 60% C8)

Polymer micelles encapsulating G-CSF were prepared in the same manner as in the test example using PEG-pGlu (10-40, 30% Chol), except that PEG-pGlu (10-40, 60% C8) was used as the block copolymer, and the number of animals for the sample was nine. The time-courses of plasma G-CSF concentration were examined.

(3) Mixed Polymer Micelles

PEG-pGlu (10-40, 30% Chol) and PEG-pGlu (10-40, 60% C8) were each weighed in an equal amount and both of the polymers were dissolved in dichloromethane and completely homogenized. After that, the solvent was removed using a shaking concentrator to produce a film. An empty micelle was then obtained in accordance with a conventional method. G-CSF was then encapsulated into the empty micelle so as to achieve a concentration of 5% (w/w) with respect to the polymers in accordance with a conventional method. The resultant polymer micelles encapsulating G-CSF were administered to rats to examine the time-courses of plasma G-CSF concentration.

(4) Direct Administration of G-CSF

The time-course of plasma G-CSF concentration was examined in the same manner as in the test example using PEG-pGlu (10-40, 30% Chol), except that a G-CSF solution (100 µg/mL) was used in place of the solution of the polymer micelles encapsulating G-CSF, and the number of animals for the sample was five.

Figure 3:
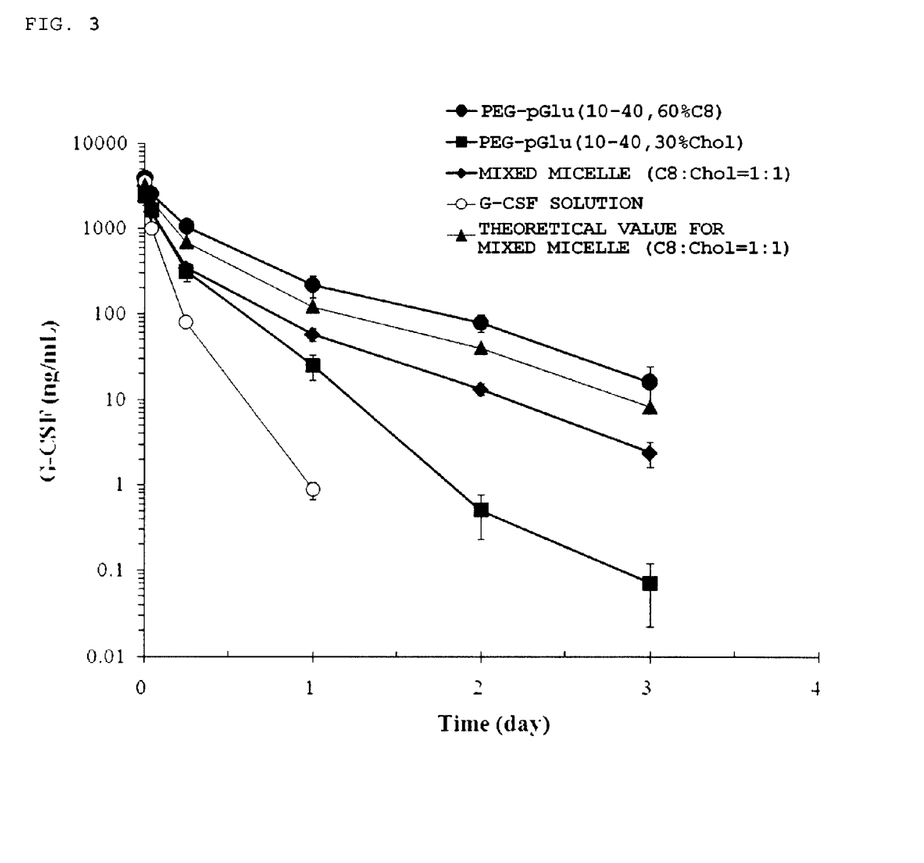
FIG. 3 is a graph illustrating the time-courses of plasma G-CSF concentration in Example 1.

FIG. 3 illustrates the results of Example 1 (average±SD). FIG. 3 also illustrates theoretical values for the time-course of plasma concentration of a mixed polymer micelle (1:1), which theoretical values were calculated from the results of the time-courses of the plasma concentration of the test examples using PEG-pGlu (10-40, 30% Chol) and PEG-pGlu (10-40, 60% C8).

As illustrated in FIG. 3, when G-CSF was directly administered, G-CSF was degraded or metabolized very rapidly and the retention time in plasma was extremely short. On the other hand, when G-CSF encapsulated in polymer micelles was administered, the retention time in plasma was greatly prolonged. In addition, polymer micelles comprised solely of block copolymers with HDL affinity had a higher rate of release of G-CSF as compared to polymer micelle comprised solely of block copolymer without HDL affinity (i.e. lower HDL affinity). Further, the mixed polymer micelles that included PEG-pGlu (10-40, 30% Chol) and PEG-pGlu (10-40, 60% C8) at a ratio of 1:1 exhibited observed values for the plasma G-CSF concentration that were markedly lower than theoretical values therefor. This revealed that a mixture of two block copolymers having different lipoprotein affinities yielded a surprising sustained drug release profile that was unexpected in view of the corresponding theoretical value.

Example 2

(1) C8-Type Micelles

PEG-pGlu (10-40, 90% C8) was used as the block copolymer. The block copolymer was weighed in a vial. A 20 mM MES Buffer (pH 5) including 13.3% sucrose was added thereto so as to achieve a polymer concentration of 10 mg/mL, and the mixture was vigorously stirred at 4° C. overnight. The polymer solution was subjected to ultrasonic irradiation (in an ice water bath, High, interval of 1 second, 15 minutes×3) using a biodisruptor (NIHONSEIKI KAISHA LTD., High Power Unit) and then treated with a 0.22-µm membrane filter. To the solution was added the above-mentioned 20 mM MES Buffer (pH 5) including sucrose, and the polymer concentration was adjusted to 2 mg/mL to obtain an empty micelle solution. To the resultant empty micelle solution (1.2 mL) was added a 300 µg/mL G-CSF solution (0.4 mL) so as to achieve a concentration of 5% (w/w) with respect to the polymer, and the mixture was inverted and swirled, left to stand still at 4° C. overnight, and then stored at −80° C. The stored mixture was thawed at room temperature before use.

(2) Bn-Type Micelles

Polymer micelles encapsulating G-CSF were prepared in the same manner as in the test example of the C8-type micelle, except that PEG-pGlu (10-40, 100% Bn) was used as the block copolymer.

(3) Mixed-Type Micelles

PEG-pGlu (10-40, 90% C8) and PEG-pGlu (10-40, 100% Bn) were each weighed in a vial and completely dissolved with acetone so as to achieve a polymer concentration of 10 mg/mL. The solutions were mixed with each other so that the weight ratios of PEG-pGlu (10-40, 90% C8) to PEG-pGlu (10-40, 100% Bn) were 19:1, 4:1, and 1:1. After that, the solvent was removed using a shaking concentrator to produce a film. Then, an empty micelle was obtained in accordance with a conventional method. Then, G-CSF was encapsulated into the empty micelle so as to achieve a concentration of 5% (w/w) with respect to the polymers in accordance with a conventional method.

These polymer micelle solutions each encapsulating G-CSF were administered to male Wistar rats (6-week-old) via the tail vein under light ether anesthesia. The dosage was 100 µg/kg of body weight and the number of animals for the sample was three for each solution. Blood was collected with a heparin-treated syringe 24 hours after the administration, and EDTA-2Na was added so that the final concentration was 1 mg/ml. In this state, the number of neutrophils was measured using a multiple automated hematology analyzer for veterinary use (pocH-100iV Diff manufactured by SYSMEX CORPORATION). Based on the resultant measured values, drug release coefficients (%) of the Bn-type micelle and various mixed-type micelles were calculated in accordance with the following equation. Table 2 shows the calculated drug release coefficients of the polymer micelles. It is believed that a larger coefficient indicates that the particular polymer micelle has a faster release rate of drug than the C8-type-only micelle.

Drug release coefficient (%)=100×($A-B$)/($A-C$)

A: Number of neutrophils in the animals to which C8-type micelle was administered
B: Number of neutrophils in the animals to which each of various mixed-type micelles was administered
C: Number of neutrophils in untreated animals

TABLE 2

| | Drug release coefficient |
|---|---|
| Bn-type micelle | 30% |
| Mixed-type micelle (C8:Bn = 1:1) | 20% |
| Mixed-type micelle (C8:Bn = 4:1) | 15% |
| Mixed-type micelle (C8:Bn = 19:1) | 19% |

As described above, also in the case where a benzyl type polymer was selected as the block copolymer with HDL affinity, the release speed of the encapsulated drug can be controlled or adjusted by employing mixed-type micelles.

Example 3

(1) C8-Type Micelle

Polymer micelles encapsulating G-CSF were prepared in the same manner as in the test example of the C8-type micelles of Example 2.

(2) Chol-Type Micelle

Polymer micelle encapsulating G-CSF were prepared in the same manner as in the test example of PEG-pGlu (10-40, 30% Chol), except that PEG-pGlu (10-40, 25% Chol) was used as the block copolymer.

(3) Mixed-Type Micelles

G-CSF was encapsulated in empty micelles in the same manner as in Example 2 except that: PEG-pGlu (10-40, 25% Chol) was used in place of PEG-pGlu (10-40, 100% Bn); dichloromethane was used as the solvent for dissolving PEG-pGlu (10-40, 90% C8); and PEG-pGlu (10-40, 90% C8) and PEG-pGlu (10-40, 25% Chol) were mixed with each other at weight ratios of 19:1 and 4:1.

The number of neutrophils was measured in the same manner as in Example 2, except that the number of animals for the sample was six. Based on the resultant measured values, drug release coefficients (%) of the Chol-type micelle and various mixed-type micelles were calculated in the same manner as in Example 2. Table 3 shows the calculated drug release coefficients of the polymer micelles.

TABLE 3

| | Drug release coefficient |
|---|---|
| Chol-type micelle | 55% |
| Mixed-type micelle (C8:Chol = 4:1) | 51% |
| Mixed-type micelle (C8:Chol = 19:1) | 26% |

As was described above, also in the case where a cholesterol type polymer was selected as the block copolymer with HDL affinity, the release speed of a drug can be controlled or adjusted by employing mixed-type micelles.

Example 4

Rat Intravenous Administration Test of Polymer Micelles Encapsulating G-CSF (1) C8-Type Micelle
Polymer micelles encapsulating G-CSF were prepared in the same manner as in the test example of the C8-type micelle of Example 2.
(2) Chol-Type Micelle
Polymer micelle encapsulating G-CSF were prepared in the same manner as in the test example of the Chol-type micelle of Example 3.
(3) Mixed Polymer Micelles
Polymer micelles each encapsulating G-CSF were prepared by mixing PEG-pGlu (10-40, 90% C8) and PEG-pGlu (10-40, 25% Chol) at weight ratios of 19:1, 4:1, and 1:1 in the same manner as in the test example of the mixed polymer micelle of Example 3.

The polymer micelle solutions each encapsulating G-CSF as obtained above were administered to male Wistar rats via the tail vein. The dosage was 100 µg/kg of body weight and the number of animals for the sample was three for each solution. Blood was collected with a heparin-treated syringe from the jugular vein under ether anesthesia 5 minutes, 1 hour, 6 hours, 1 day, 2 days, and 3 days after the administration, and the plasma G-CSF concentration was measured using a G-CSF-ELISA kit (manufactured by Ray Biotech, Inc.).

Figure 4:
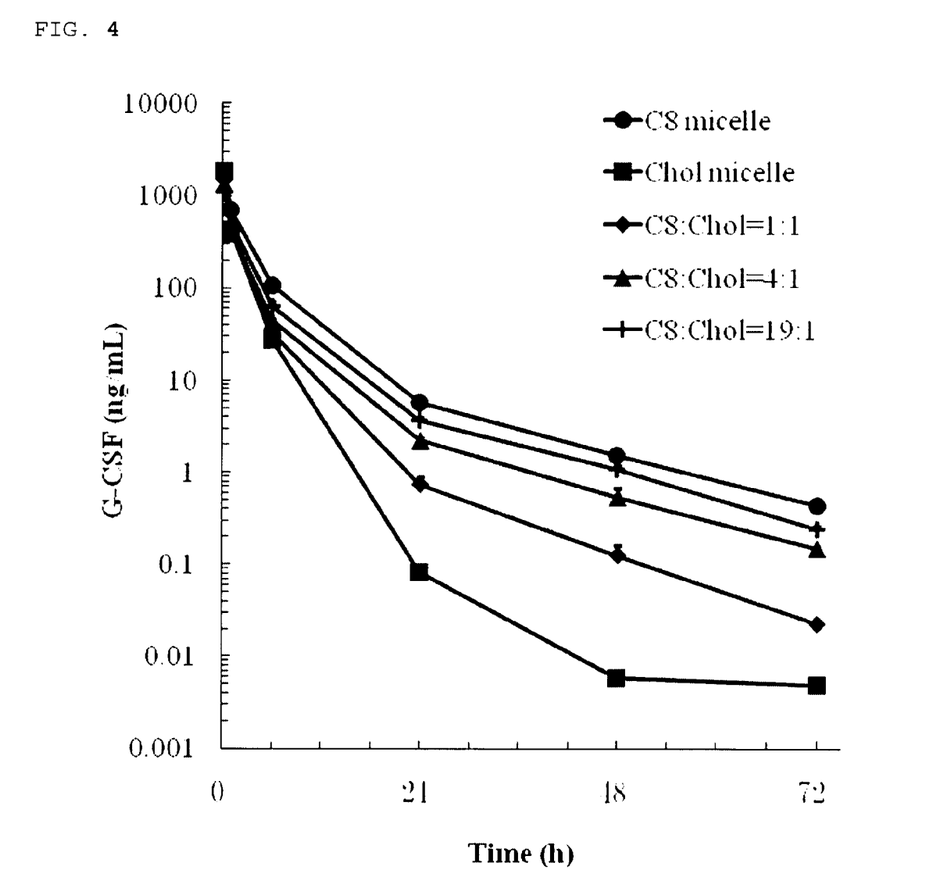
FIG. 4 is a graph illustrating the time-courses of plasma G-CSF concentration in Example 4.

FIG. 4 illustrates the results of Example 4. As can be seen from FIG. 4, also in this example, the retention time of a drug in plasma can be controlled or adjusted; in other words, the release rate of a drug can be controlled or adjusted by employing a mixed-type micelle. It should be noted that, also in this example, observed values for the plasma G-CSF concentration were markedly lower than theoretical values therefor in any of the mixed-type micelles.

The invention claimed is:

1. A pharmaceutical composition comprising:
a polymer micelle composition; and
a drug encapsulated in the polymer micelle composition, the drug having a molecular weight of 1,500 or more and being selected from the group consisting of water-soluble physiologically active polypeptides and water-soluble physiologically active proteins,
wherein:
the polymer micelle composition comprises a plurality of first block copolymers and a plurality of second block copolymers, each having a hydrophobic polymer chain segment and a hydrophilic polymer chain segment, the first and second block copolymers being arranged in a state in which the respective hydrophobic polymer chain segments are directed radially inward and the respective hydrophilic polymer chain segments are directed radially outward;
the first block copolymers have a greater affinity for HDL than the second block copolymers;
the hydrophobic polymer chain segment of the first block copolymers comprises a polyamino acid including repeating units of a hydrophobic derivative of an amino acid, wherein the amino acid derivative comprises a side chain to which a sterol residue is covalently attached;
the hydrophobic polymer chain segment of the second block copolymers comprises a polyamino acid including repeating units of a hydrophobic derivative of an amino acid, wherein the amino acid derivative comprises a side chain to which a hydrophobic group having a linear or branched structure is bound; and
detachment of the first block copolymers from the polymer micelle composition is inducible by adhesion of the first block copolymers to HDL, such that at least one gap formed by the detachment of the first block copolymers permits release of the encapsulated drug, which is not bound to the first or second block copolymers, through the at least one gap and the second block copolymers promote resealing of the at least one gap.

2. A pharmaceutical composition comprising:
a polymer micelle composition; and
a drug encapsulated in the polymer micelle composition, the drug having a molecular weight of 1,500 or more and being selected from the group consisting of water-soluble physiologically active polypeptides and water-soluble physiologically active proteins,
wherein:
the polymer micelle composition comprises block copolymers each having a hydrophobic polymer chain segment and a hydrophilic polymer chain segment, a plurality of the block copolymers being arranged in a state in which the respective hydrophobic polymer chain segments are directed radially inward and the respective hydrophilic polymer chain segments are directed radially outward;
at least some of the block copolymers have an affinity for HDL;
a hydrophobic polymer chain segment of the block copolymers having an affinity for HDL comprises a polyamino acid including repeating units of a hydrophobic derivative of an amino acid, wherein the amino acid derivative comprises a side chain to which a sterol residue is covalently attached;
the hydrophilic polymer chain segment of the block copolymer having affinity for HDL is comprised of poly(ethylene glycol); and
detachment of the block copolymers having affinity for HDL is inducible by adhesion to HDL, such that at least one gap formed by the detached block copolymer(s) permits release of the encapsulated drug, which is not bound to the block copolymers, through the at least one gap.

3. The pharmaceutical composition according to claim 1, wherein the hydrophobic derivative of an amino acid in the hydrophobic polymer chain segment of the first or second block copolymers comprises a derivative of an acidic amino acid selected from the group consisting of aspartic acid and glutamic acid.

4. The pharmaceutical composition according to claim 1, wherein the hydrophobic group having a linear or branched structure comprises a $C_4$ to $C_{18}$ unsubstituted or substituted linear or branched alkyl group, a $C_4$ to $C_{18}$ unsubstituted or substituted linear or branched alkenyl group, or a $C_4$ to $C_{18}$ unsubstituted or substituted linear or branched alkynyl group.

5. The pharmaceutical composition according to claim 1, wherein the hydrophobic polymer chain segment of the second block copolymer comprises a derivative of an acidic amino acid selected from aspartic acid and glutamic acid.

6. The pharmaceutical composition according to claim 2, wherein the hydrophobic derivative of an amino acid comprises a derivative of an acidic amino acid selected from the group consisting of aspartic acid and glutamic acid.

7. The pharmaceutical composition according to claim 3, wherein the hydrophobic group having a linear or branched structure comprises a $C_4$ to $C_{18}$ unsubstituted or substituted linear or branched alkyl group, a $C_4$ to $C_{18}$ unsubstituted or substituted linear or branched alkenyl group, or a $C_4$ to $C_{18}$ unsubstituted or substituted linear or branched alkynyl group.

8. The pharmaceutical composition according to claim 3, wherein the hydrophobic derivative of an amino acid in the second block copolymer comprises a derivative of an acidic amino acid selected from the group consisting of aspartic acid and glutamic acid.

9. The pharmaceutical composition according to claim 4, wherein the hydrophobic derivative of an amino acid in the second block copolymer comprises a derivative of an acidic amino acid selected from the group consisting of aspartic acid and glutamic acid.

10. The pharmaceutical composition according to claim 8, wherein the hydrophobic derivative of an amino acid in the second block copolymer comprises a derivative of an acidic amino acid selected from the group consisting of aspartic acid and glutamic acid.

11. A pharmaceutical composition, comprising:
a polymer micelle composition; and
a drug encapsulated in, but not bound to, the polymer micelle composition, the drug having a molecular weight of at least 1,500 and being a water-soluble, physiologically-active polypeptide or a water-soluble, physiologically-active protein,
wherein:
the polymer micelle composition comprises a plurality of block copolymers each having a hydrophobic polymer chain segment and a hydrophilic polymer chain segment, wherein the block copolymers are arranged such the respective hydrophobic polymer chain segments are located radially inward and the respective hydrophilic polymer chain segments are located radially outward;
at least some of the block copolymers have an affinity for HDL; and
the hydrophobic polymer chain segment of the block copolymers having an affinity for HDL comprises a polyamino acid including repeating units derived from a hydrophobic derivative of at least one amino acid having a side chain, the hydrophobic derivative formed by attachment of a sterol residue to the amino acid side chain.

12. The pharmaceutical composition according to claim 11, wherein the hydrophilic polymer chain segment of the block copolymers having an affinity for HDL comprises poly(ethylene glycol).

13. The pharmaceutical composition according to claim 12, wherein at least some of the block copolymers have a lesser affinity for HDL than the block copolymers having sterol residues bound thereto.

14. The pharmaceutical composition according to claim 13, wherein the hydrophobic polymer chain segment of the block copolymers having a lesser affinity for HDL comprises a polyamino acid including repeating units of a hydrophobic derivative of an amino acid, the hydrophobic derivative formed by attachment of a hydrophobic group having a linear or branched structure to the amino acid side chain.

15. The pharmaceutical composition according to claim 14, wherein the hydrophobic group having a linear or branched structure is selected from the group consisting of a $C_4$ to $C_{18}$ unsubstituted or substituted linear or branched alkyl group, a $C_4$ to $C_{18}$ unsubstituted or substituted linear or branched alkenyl group, and a $C_4$ to $C_{18}$ unsubstituted or substituted linear or branched alkynyl group.

16. The pharmaceutical composition according to claim 15, wherein the repeating units derived from the hydrophobic derivative of the amino acid having a sterol residue bound thereto are between 10 and 100 mol % of all of repeating units that form the hydrophobic polymer chain segment of the block copolymers having an affinity for HDL.

17. The pharmaceutical composition according to claim 16, wherein the repeating units derived from the hydrophobic derivative of the amino acid having a sterol residue bound thereto are between 20 and 80 mol % of all of repeating units that form the hydrophobic polymer chain segment of the block copolymers having an affinity for HDL.

18. The pharmaceutical composition according to claim 17, wherein each of the plurality of block copolymers comprises between 10 and 2,500 ethylene glycol units in its hydrophilic polymer chain segment and between 10 and 300 amino acid units in its hydrophobic polymer chain segment.

19. The pharmaceutical composition according to claim 18, wherein the block copolymers having an affinity for HDL exhibit an HDL transfer rate of at least 30% and the block copolymers having a lesser affinity for HDL exhibit an HDL transfer rate of less than 30%.

20. The pharmaceutical composition according to claim 19, wherein a weight ratio of (i) the block copolymers having an affinity for HDL to (ii) the block copolymers having a lesser affinity for HDL is between 15:85 and 85:15.

21. The pharmaceutical composition according to claim 20, wherein the drug is selected from the group consisting of interferon α, β, and γ, erythropoietin, G-CSF, growth hormone, interleukins, tumor necrosis factor, granulocyte-macrophage colony-stimulating factor, macrophage colony-stimulating factor, hepatocyte growth factor, TGF-β superfamily, EGF, FGF, IGF-I, and blood coagulation factors.

22. A method of treating a patient in need thereof comprising intraveneously administering to the patient a therapeutically effective amount of the pharmaceutical composition of claim 11.

* * * * *

UNITED STATES PATENT AND TRADEMARK OFFICE
CERTIFICATE OF CORRECTION

PATENT NO. : 8,574,601 B2
APPLICATION NO. : 13/258797
DATED : November 5, 2013
INVENTOR(S) : Yasuki Kato et al.

It is certified that error appears in the above-identified patent and that said Letters Patent is hereby corrected as shown below:

In the Claims:

Column 19, line 27, change "according to claim 8" to "according to claim 7".

Signed and Sealed this
Thirteenth Day of May, 2014

Michelle K. Lee
*Deputy Director of the United States Patent and Trademark Office*